United States Patent
Corvi et al.

(10) Patent No.: US 6,638,233 B2
(45) Date of Patent: Oct. 28, 2003

(54) APPARATUS AND METHODS FOR MATERIAL CAPTURE AND REMOVAL

(75) Inventors: Tim Corvi, Belmont, CA (US); Stephen Boyd, Moss Beach, CA (US); Brett Follmer, Santa Clara, CA (US); John G. Stine, San Jose, CA (US); David W. Snow, San Carlos, CA (US); Darren G. Doud, San Jose, CA (US)

(73) Assignee: Fox Hollow Technologies, Inc., Redwood City, CA (US)

(*) Notice: Subject to any disclaimer, the term of this patent is extended or adjusted under 35 U.S.C. 154(b) by 0 days.

(21) Appl. No.: 09/377,884

(22) Filed: Aug. 19, 1999

(65) Prior Publication Data
US 2002/0038097 A1 Mar. 28, 2002

(51) Int. Cl.[7] ............................................... A61B 10/00
(52) U.S. Cl. ...................................... 600/564; 606/182
(58) Field of Search ................................ 600/562, 564, 600/566, 570; 606/182, 183, 171

(56) References Cited

U.S. PATENT DOCUMENTS

| | | |
|---|---|---|
| 2,178,790 A | 11/1939 | Henry |
| 3,705,577 A | 12/1972 | Sierra |
| 3,815,604 A | 6/1974 | O'Malley et al. |
| 3,837,345 A | 9/1974 | Matar |
| 3,995,619 A | 12/1976 | Glatzer |
| 4,210,146 A | 7/1980 | Banko |
| 4,696,298 A | 9/1987 | Higgins et al. |
| 4,781,186 A | 11/1988 | Simpson et al. |
| 4,819,635 A | 4/1989 | Shapiro |
| 4,850,957 A | 7/1989 | Summers |
| RE33,258 E | 7/1990 | Onik et al. |
| 4,979,951 A | 12/1990 | Simpson |
| 4,994,067 A | 2/1991 | Summers |
| 5,024,651 A | 6/1991 | Shiber |
| 5,087,265 A | 2/1992 | Summers |
| 5,224,488 A | 7/1993 | Neuffer |
| 5,226,910 A | 7/1993 | Kajiyama et al. |
| 5,242,460 A | 9/1993 | Klein et al. |
| 5,250,059 A | 10/1993 | Andreas et al. |
| 5,250,065 A | 10/1993 | Clement et al. |
| 5,285,795 A | 2/1994 | Ryan et al. |
| 5,312,425 A | 5/1994 | Evans et al. |
| 5,318,528 A | 6/1994 | Heaven et al. |
| 5,395,313 A | 3/1995 | Naves et al. |
| 5,419,774 A * | 5/1995 | Willard et al. ................. 604/22 |
| 5,431,673 A | 7/1995 | Summers et al. |
| 5,505,210 A | 4/1996 | Clement |
| 5,507,292 A | 4/1996 | Jang et al. |
| 5,571,122 A | 11/1996 | Kelly et al. |
| 5,571,130 A | 11/1996 | Simpson et al. |

(List continued on next page.)

*Primary Examiner*—Max F. Hindenburg
*Assistant Examiner*—Pamela Wingood
(74) *Attorney, Agent, or Firm*—Townsend and Townsend and Crew, LLP

(57) ABSTRACT

Catheters, kits, and methods are provided for removing material from a body lumen. The catheters and methods may be used in a variety of body lumens, including but not limited to coronary and other arteries. In general, the catheter has a cutting element that cuts material while the material is engaged by a material capture device on the catheter body. Preferably, the material capture device tensions the material during cutting, which reduces the amount of cutting force required. The material capture device typically follows a path that draws material into the catheter body. Preferably, but not necessarily, the material capture device may be arranged on the catheter body to advance along a path outwardly from the catheter body into the material and then inwardly towards the catheter body to tension the material. The cutting element on the catheter body moves between a first position and a second position to cut the material while in tension.

63 Claims, 15 Drawing Sheets

U.S. PATENT DOCUMENTS

| | | |
|---|---|---|
| 5,584,842 A | 12/1996 | Fogarty et al. |
| 5,620,447 A | 4/1997 | Smith et al. |
| 5,634,464 A | 6/1997 | Jang et al. |
| 5,665,098 A | 9/1997 | Kelly et al. |
| 5,674,232 A | 10/1997 | Halliburton |
| 5,695,506 A | 12/1997 | Pike |
| 5,709,698 A | 1/1998 | Adams et al. |
| 5,733,296 A | 3/1998 | Rogers et al. |
| 5,843,103 A | 12/1998 | Wulfman |
| 6,027,514 A * | 2/2000 | Stine et al. ................. 606/159 |
| 6,036,656 A | 3/2000 | Slater |
| 6,036,707 A | 3/2000 | Spaulding |

* cited by examiner

APPARATUS AND METHODS FOR MATERIAL CAPTURE AND REMOVAL

BACKGROUND OF THE INVENTION

The present invention relates generally to apparatus and methods for removing occluding materials from body lumens. More particularly, the present invention relates to the construction and use of atherectomy catheters for excising atheroma and other materials from blood vessels.

Cardiovascular disease frequently arises from the accumulation of atheromatous material on the inner walls of vascular lumens, particularly arterial lumens of the coronary and other vasculature, resulting in a condition known as atherosclerosis. Atherosclerosis occurs naturally as a result of aging, but may also be aggravated by factors such as diet, hypertension, heredity, vascular injury, and the like. Atheromatous and other vascular deposits restrict blood flow and can cause ischemia which, in acute cases, can result in myocardial infarction. Atheromatous deposits can have widely varying properties, with some deposits being relatively soft and others being fibrous and/or calcified. In the latter case, the deposits are frequently referred to as plaque.

Atherosclerosis can be treated in a variety of ways, including drugs, bypass surgery, and a variety of catheter-based approaches which rely on intravascular widening or removal of the atheromatous or other material occluding a blood vessel. Of particular interest to the present invention, a variety of methods for cutting or dislodging material and removing such material from the blood vessel have been proposed, generally being referred to as atherectomy procedures. Atherectomy catheters intended to excise material from the blood vessel lumen generally employ a rotatable and/or axially translatable cutting blade which can be advanced into or past the occlusive material in order to cut and separate such material from the blood vessel lumen. In particular, side-cutting atherectomy catheters generally employ a housing having an aperture on one side, a blade which is rotated or translated by the aperture, and a balloon or other deflecting structure to urge the aperture against the material to be removed.

Although atherectomy catheters have proven to be very successful in treating many types of atherosclerosis, some catheter designs suffer from certain limitations. For example, many side-cutting atherectomy catheters have difficulty in capturing occluding material in the cutting aperture. To facilitate material capture, the cutting aperture is frequently elongated. Although improving material capture, such lengthening makes it more difficult to introduce the distal end of the catheter through torturous regions of the vasculature. Additionally, it is often difficult for conventional atherectomy cutters to apply the requisite pressure to cut off the targeted material. When higher pressures are applied, damage to the artery (barotrauma) can occur. High pressures can also compress plaque, subsequently reducing the cutter's ability to capture the occlusive material. This decreases the effectiveness of these cutters and limits the cutter and catheter designs.

For these reasons, it is desired to provide atherectomy catheters which can access small, tortuous regions of the vasculature and which can remove atheromatous and other occluding materials from within blood vessels in a controlled fashion with minimum risk of injuring the blood vessel wall. In particular, it is desired to provide atherectomy catheters which can facilitate capturing of occlusive material. It would also be particularly desirable to decrease the amount of force required to cut off occlusive material from the body. At least some of these objectives will be met by the catheter and method of the present invention described hereinafter and in the claims.

SUMMARY OF THE INVENTION

The present invention provides catheters, kits, and methods for removing material from a body lumen. The catheters and methods of the present invention are for use in a variety of body lumens, including but not limited to intravascular lumens such as the coronary artery and other blood vessels. In general, the catheter of the present invention has a cutting element that cuts material engaged by a material capture device on the catheter body. Preferably, the material capture device tensions the material during cutting, which reduces the amount of cutting force required. The material capture device typically follows a path that draws material into the catheter body. Preferably, but not necessarily, the material capture device is arranged on the catheter body to advance along a path outwardly from the catheter body into the material and then inwardly towards the catheter body to tension the material. In some embodiments, the material capture device may extend in an outwardly direction but not beyond the outer diameter of the catheter body. The cutting element on the catheter body moves between a first position and a second position to cut the material while in tension, where motion of the cutting element urges the material capture device to draw cut material into the catheter body.

Desirably, the blade or blades of the catheter will be actuable with the application of reasonable mechanical forces which are capable of being transmitted along even rather lengthy catheters. Further desirably, the catheters will be suitable for directional removal of occluding material and may include mechanisms for engaging cutting blades against selected portions of a vascular wall. Optionally, the engaging mechanisms should permit blood perfusion during performance of an atherectomy procedure.

In one embodiment, the catheter of the present invention uses a material capture device in the form of a material capture needle. The needle will be deployed in a radially outward direction from the catheter body. Preferably, but not necessarily, the needle will capture material while the catheter remains stationary. Some embodiments may use a plurality of material capture needles. The material capture needle may follow a path outwardly from the catheter body in various manners. In one embodiment, the needle has a portion that advances through an elongate slot on the catheter body to move the needle along a path outwardly from the catheter body. Another embodiment uses a curved needle rotatably mounted about a pivot pin. As the needle is rotated, it will protrude outwardly from the catheter body. A preferred embodiment uses a needle having a bias element which urges the needle outwardly when the catheter is in position. Typically, a material cutting element will engage the material that has been captured and sheer off the material into the catheter.

In a further embodiment, a material capture device of the present invention uses a penetrating member mounted to extend through an aperture on the catheter body to penetrate material in advance of the cutting blade and to draw material into the catheter body as the cutting blade is advanced past the aperture. The penetrating member is rotatably mounted to the slidable cutting blade on the catheter body. A cam surface on the catheter body engages a surface of the penetrating member to guide the member along a path to engage the material and draw the material into the catheter body. In a still further embodiment, an abutment or raised portion on the catheter body is mounted to engage one end of the penetrating member. This contact caused the penetrating member to rotate about its pivot point on the cutting blade and thus engage material and draw material into the catheter body.

In another aspect of the present invention, a method is provided for excising occlusive material from within a body lumen. The method involves engaging the occlusive material with a material capture device on a catheter body. The material is drawn in a radially inward direction by the device to tension the material to be cut. A blade is advanced through the tensioned material to sever the material from the body lumen. As mentioned previously, tensioning the material reduces the amount of cutting force required. The tensioning of the occlusive material may also comprise moving the material capture device towards a catheter body while the material capture device is in contact with the occlusive material. Typically, the engaging and tensioning steps may also be performed with a single motion by the user to facilitate cutting.

In a still further aspect, kits according to the present invention will comprise a catheter having a material capture device. The kits will further include instructions for use setting forth a method as described above. Optionally, the kits will further include packaging suitable for containing the catheter and the instructions for use. Exemplary containers include pouches, trays, boxes, tubes, and the like. The instructions for use may be provided on a separate sheet of paper or other medium. Optionally, the instructions may be printed in whole or in part on the packaging. Usually, at least the catheter will be provided in a sterilized condition. Other kit components, such as a guidewire, may also be included.

A further understanding of the nature and advantages of the invention will become apparent by reference to the remaining portions of the specification and drawings.

DESCRIPTION OF THE SPECIFIC EMBODIMENTS

Figure 1:
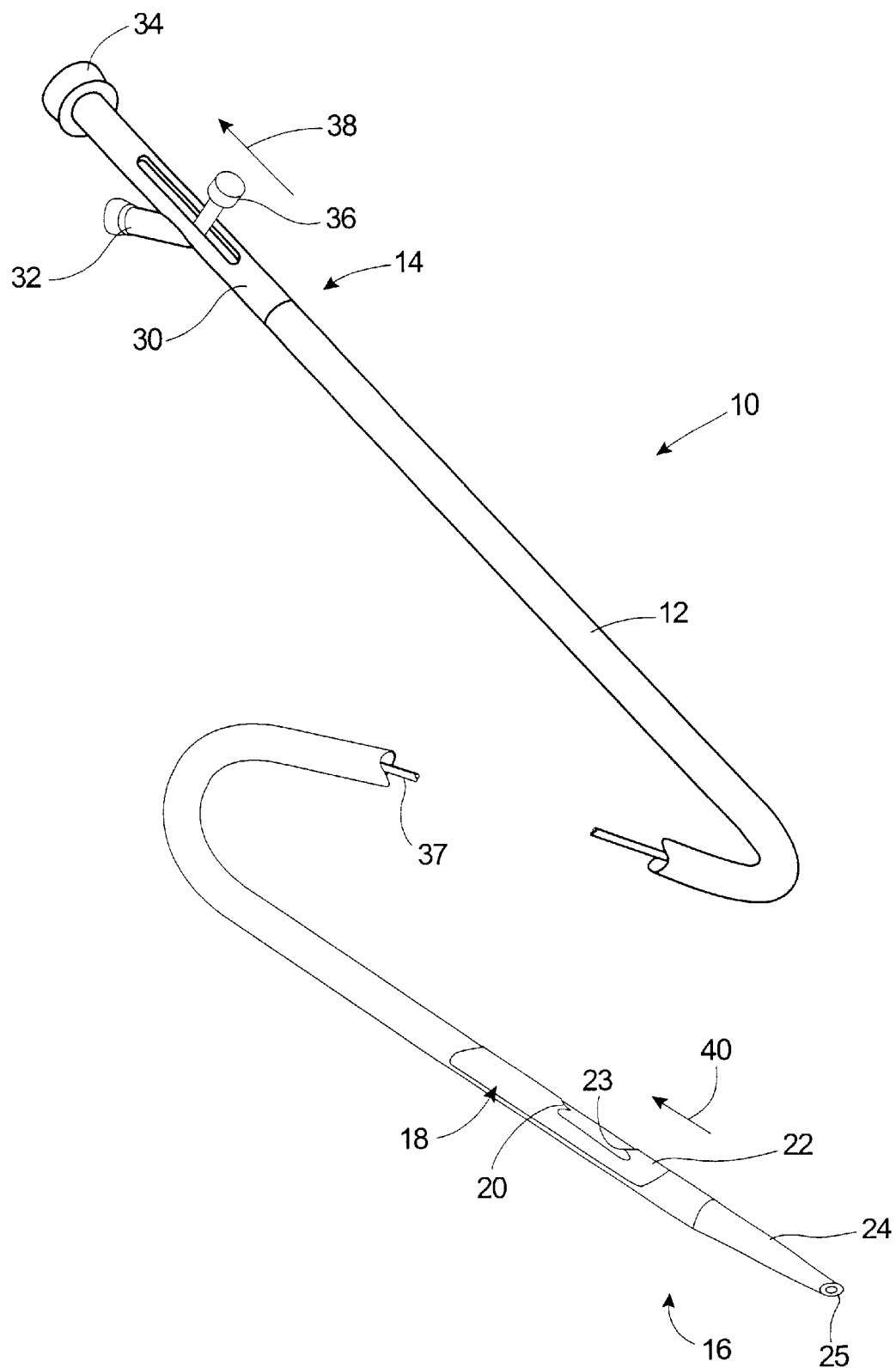
FIG. 1 is a perspective view of an atherectomy catheter constructed in accordance with the principles of the present invention.

The present invention provides devices, methods, and kits for use in removing material from a body lumen. The present invention may be used in a variety of body lumens, including but not limited to coronary and other arteries. Advantageously, the present invention reduces the amount of force required to cut material and facilitates material capture into apertures of the catheter.

Apparatus according to the present invention will comprise catheters having catheter bodies adapted for intraluminal introduction to the target body lumen. The dimensions and other physical characteristics of the catheter bodies will vary significantly depending on the body lumen which is to be accessed. In the exemplary case of atherectomy catheters intended for intravascular introduction, the catheter bodies will typically be very flexible and suitable for introduction over a guidewire to a target site within the vasculature. In particular, catheters can be intended for "over-the-wire" introduction when a guidewire lumen extends fully through the catheter body or for "rapid exchange" introduction where the guidewire lumen extends only through a distal portion of the catheter body.

Catheter bodies intended for intravascular introduction will typically have a length in the range from 50 cm to 200 cm and an outer diameter in the range from 1 French (0.33 mm; Fr.) to 12 Fr., usually from 3 Fr. to 9 Fr. In the case of coronary catheters, the length is typically in the range from 125 to 200 cm, the diameter is preferably below 8 Fr., more preferably below 7 Fr., and most preferably in the range from 2 Fr. to 7 Fr. Catheter bodies will typically be composed of an organic polymer which is fabricated by conventional extrusion techniques. Suitable polymers include polyvinylchloride, polyurethanes, polyesters, polytetrafluoroethylenes (PTFE), silicone rubbers, natural rubbers, and the like. Optionally, the catheter body may be reinforced with braid, helical wires, axial filaments, or the like, in order to increase rotational strength, column strength, toughness, pushability, and the like. Suitable catheter bodies may be formed by extrusion, with one or more lumens being provided when desired. The catheter diameter can be modified by heat expansion and shrinkage using conventional techniques. The resulting catheters will thus be suitable for introduction to the vascular system, often the coronary arteries, by conventional techniques.

The cutting blades used in the present invention will usually be formed from a metal, but could also be formed from hard plastics, ceramics, or composites of two or more materials, which can be honed or otherwise formed into the desired cutting edge. In the exemplary embodiments, the cutting blades are formed as coaxial tubular blades with the cutting edges defined in aligned apertures therein. It will be appreciated that the present invention is not limited to such preferred cutting blade assemblies, in a variety of other designs, such as the use of wiper blades, scissor blades or the like. Optionally, the cutting edge of either or both the blades may be hardened, e.g., by application of a coating. A preferred coating material is titanium nitride, available from Brycoat, Inc., which may be applied according to manufacturer's instructions.

Referring now to FIG. 1, a catheter 10 constructed in accordance with the principles of the present invention comprises a catheter body 12 having a proximal end 14 and a distal end 16. A cutting mechanism 18 comprises an outer cutter 20, an inner cutter 22 is attached to the distal end of the catheter body 12, and a needle 23 as a material capture device. An atraumatic tip 24 is attached to the distal end of the outer cutter 20, and a guidewire lumen 25 extends through the entire catheter body, cutting mechanism 18, and terminates in port 25 at the distal tip of tip section 24. A proximal hub 30 is attached to the proximal end of catheter body 12 and comprises a perfusion/aspiration connector 32, a guidewire connector 34, and a slider 36. The slider 36 is attached to the proximal end of an actuator rod 37 which extends from the hub 30 through the lumen of catheter body 12 into the cutting mechanism 18 where it is attached at a proximal end of the inner cutter 22. In this way, manual actuation of slider 36 in the direction of arrow 38 moves inner cutter 22 in the direction of arrow 40.

Figure 2A:
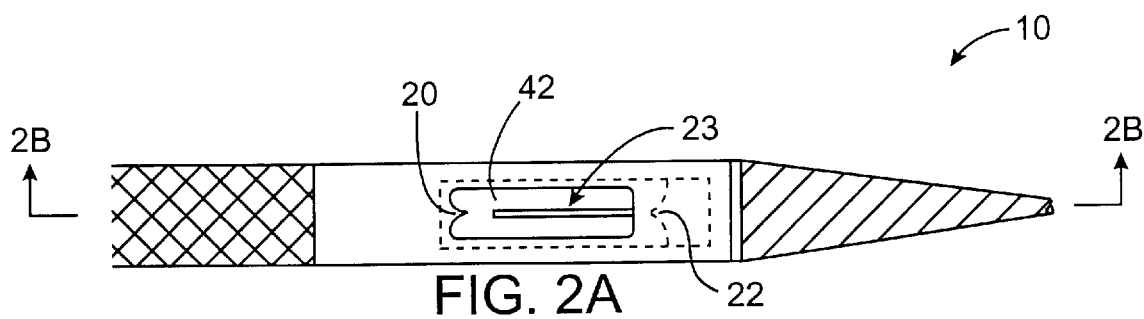
FIGS. 2–4 show various embodiments of a material capture device and a material cutting element according to the present invention.
Figure 2B:
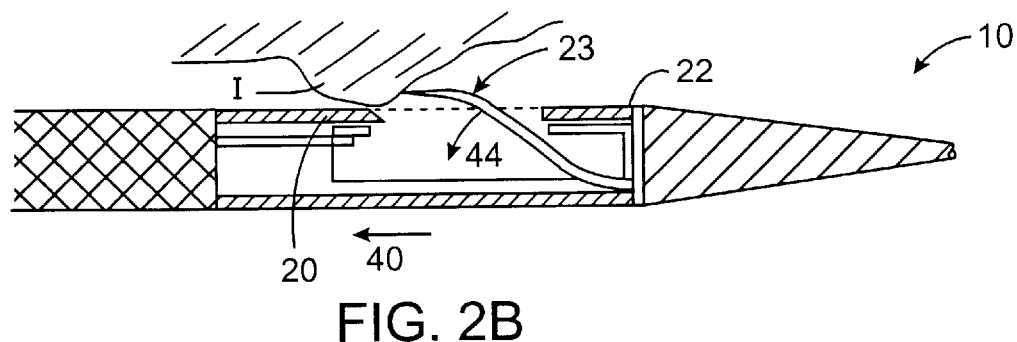

Referring to FIGS. 2A and 2B, this embodiment of the catheter 10 uses the material capture needle 23 to capture the material and tension it towards the cutters 20 and 22. The material capture needle 23 follows a path where the material capture needle extends outwardly from the catheter body and moves inwardly towards the catheter body to tension the material. In this embodiment, when the material capture needle 23 is deployed, it angles out from the aperture 42 and a portion of the material capture needle typically runs parallel to the window with the sharpened tip located near the proximal end of the aperture. The inner cutter or cutting element 22 is reciprocated to open and close the aperture 42 formed in the wall of the catheter body 12. Movement of the inner cutter 22 also controls the deployment of the material capture needle. When the inner cutter 22 opens the aperture 42, the material capture needle 23 is biased outwardly from the catheter body 12. The material capture needle 23 is preferably spring-loaded, where in its resting condition, the material capture needle extends outwardly from the catheter body 12. The material capture needle 23 is otherwise constrained within the catheter body 12 when the inner cutter 22 closes aperture 42. The material capture needle 23 may be made of a variety of materials such as stainless steel or a superelastic material.

With the material capture needle 23 deployed as shown in FIG. 2B, the material capture needle may penetrate into the material when the catheter body 12 is pulled in the proximal direction. The inner cutter 22 is then closed, as indicated by arrow 40, to push the material capture needle 23 towards the catheter body 12 as indicated by arrow 44. Preferably, closing of cutter 22 will tension the material and draw it into the catheter body 12 when the cutters 20 and 22 will shear off the material. It is also preferred that the inner cutter 22, upon finishing the closing motion, will wipe the piece of cut-off material off the material capture needle 23 and into the catheter for storage. The material capture needle 23 and cutting mechanism 18 may then be readied to make a subsequent cut. The material capture needle 23 typically has a diameter between about 0.1 to 0.5 mm, preferably 0.2 to 0.3 mm, with a length between about 1 to 5 mm, preferably 3 to 4 mm.

Figure 3A:
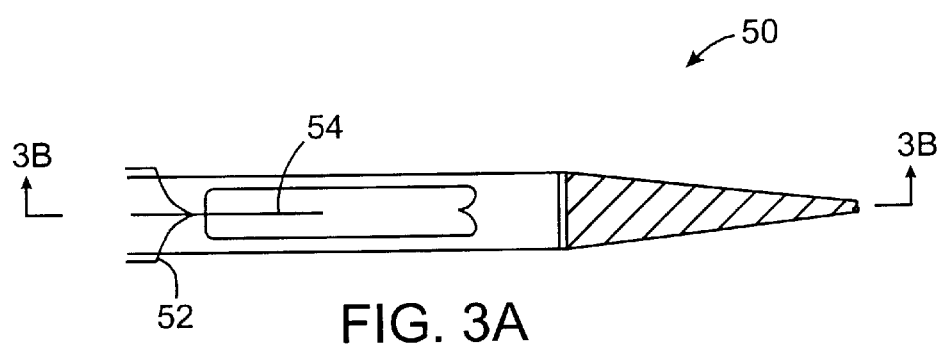
Figure 3B:
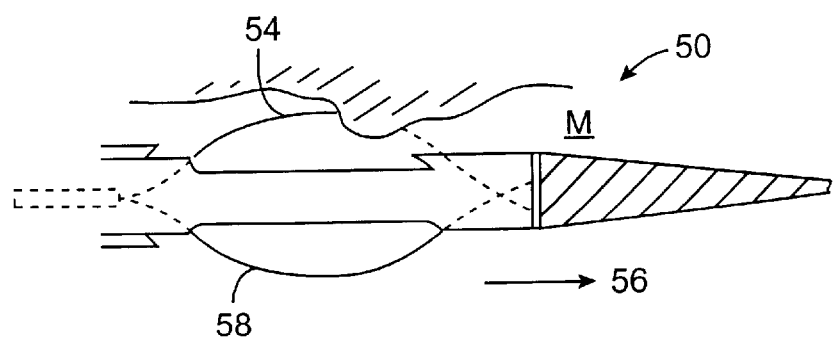

Referring to FIGS. 3–4, a variety of catheter embodiments may incorporate a needle as a material capture device. Like the catheter of FIG. 2, these catheters rely on the motion of a cutter to control positioning of the material capture needle during cutting. The FIGS. 3A–3B show the distal portion of a catheter 50 having an outer cutter 52 which reciprocates to control the deployment of the material capture needle 54. Additionally, in this embodiment, the material capture needle 54 is deployed to have a forward pointing sharpened tip. With the material capture needle 54 deployed, the catheter 50 would be pushed forward as indicated by arrow 56 to penetrate target material T. The catheter 50 may also incorporate a ski mechanism 58 to urge the cutting side of the catheter radially against the target material T. Such a ski mechanism is described in detail in commonly assigned, copending U.S. patent application Ser. No. 08/982,231 filed Dec. 17, 1997, the full disclosure of which is incorporated herein by reference. All of the catheter structures herein may optionally employ such mechanisms.

Figure 4A:
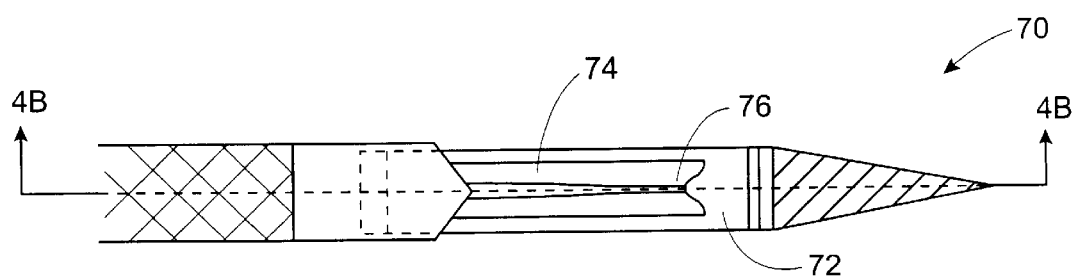
Figure 4B:
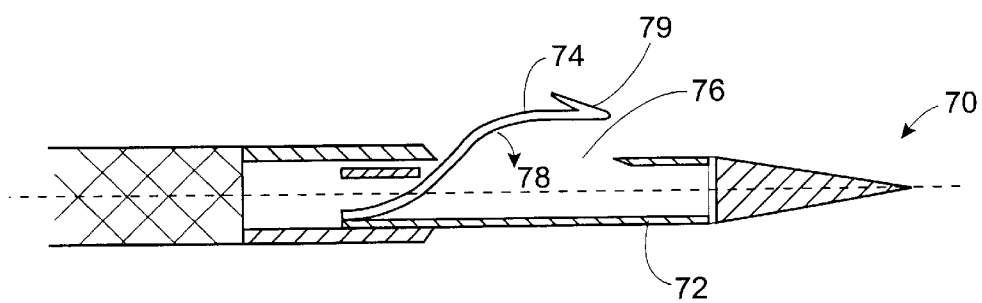

FIGS. 4A and 4B show a catheter 70 having a telescoping cutter 72 for use with a material capture needle 74. The telescoping cutter 72 is used to decrease the rigid length of the catheter 70 and may be used to create a larger window or aperture 76 for removing greater amounts of material. As the telescoping cutter 72 is drawn proximally, the material capture needle 74 will be pushed into the aperture 76 as indicated by arrow 78, along with material attached to the material capture needle. As seen in FIG. 4B, the material capture device 74 may also include one or more barbs 79 which keep the material from sliding off once it is excised.

The catheter 70 is quite useful and an improvement over conventional atherectomy catheters even without incorporation of the material capture needle 74. The decrease in the rigid length of the distal portion of catheter 70 is a significant advantage, particularly when the catheter is introduced to the highly tortuous regions of the coronary vasculature. Once at a desired location, however, the rigid cutter portion of the catheter can be extended in length by 50% or more, with a theoretical limit of 100% for a two-portion telescoping region. In the illustrated embodiment, the cutting aperture 76 is defined only on one of the cutter blades. In other embodiments, it will possible to define the aperture on both of the cutting blades and/or in a variety of configurations. While the cutting blades will preferably employ the cutting edges at each end, the advantages of the telescoping cutter can be enjoyed even without the cutting edges.

Figure 5A:
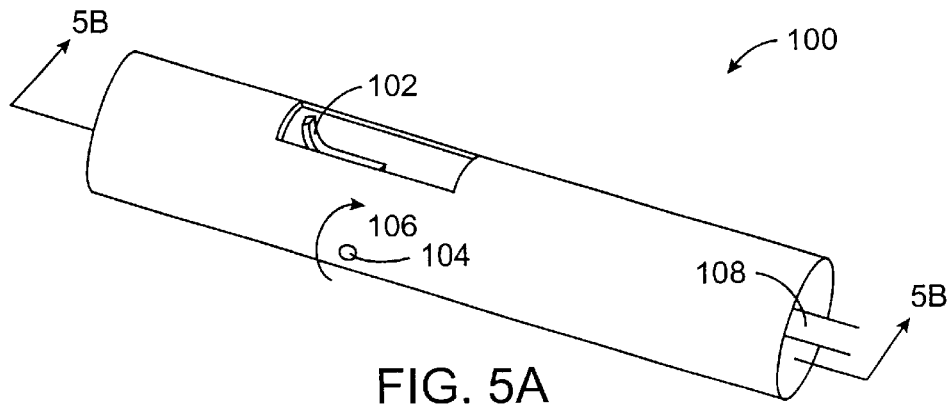
FIGS. 5A–5C illustrate a material cutting sequence using one embodiment of a material capture device and material cutting element according to the present invention.
Figure 5B:
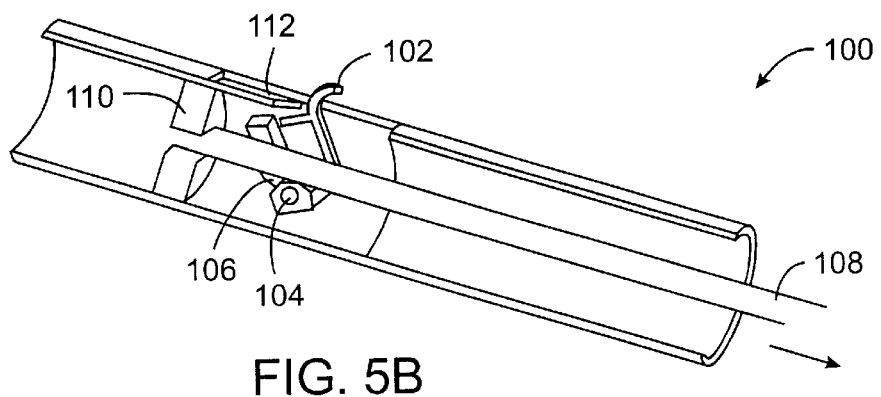
Figure 5C:
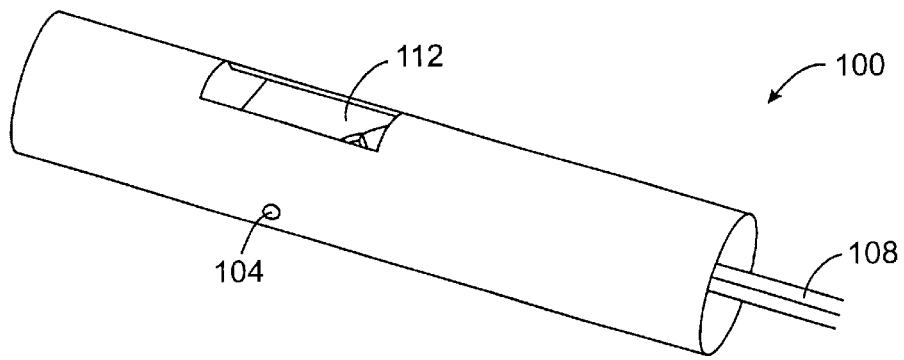

Referring now to FIGS. 5A–5C, another embodiment of an atherectomy catheter 100 uses a material capture needle 102 which rotates about a pivot pin 104. As indicated by arrow 106 in FIG. 5A, the material capture needle 102 will rotate upward as the drawbar 108 is pulled proximally. As seen in the cross-section of FIG. 5B, the drawbar 108 is coupled to slider 110 which has cutting blade 112. A cam 106 about the pivot pin 104 will pull against the material capture needle 102 as drawbar 108 is moved. The drawbar 108 will be retracted until the blade 112, as shown in FIG. 5C, has sheared off any material captured by the material capture needle 102.

Figure 6A:
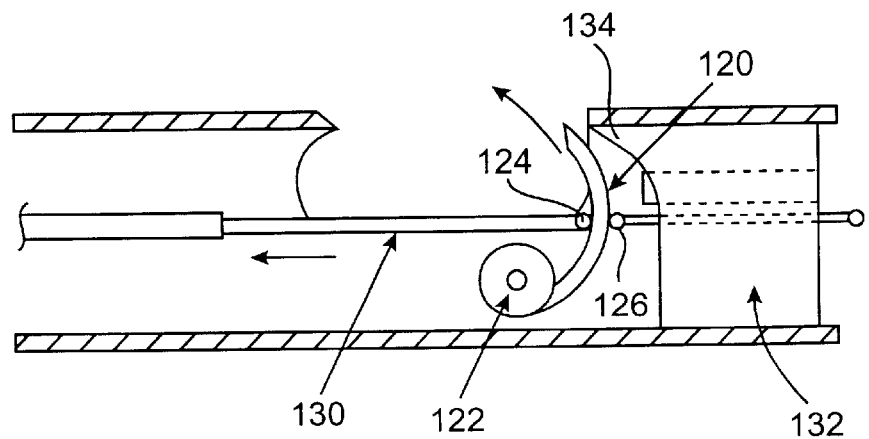
FIGS. 6A–6B show cross-sectional views of a further embodiment of a material capture device and material cutting element.
Figure 6B:
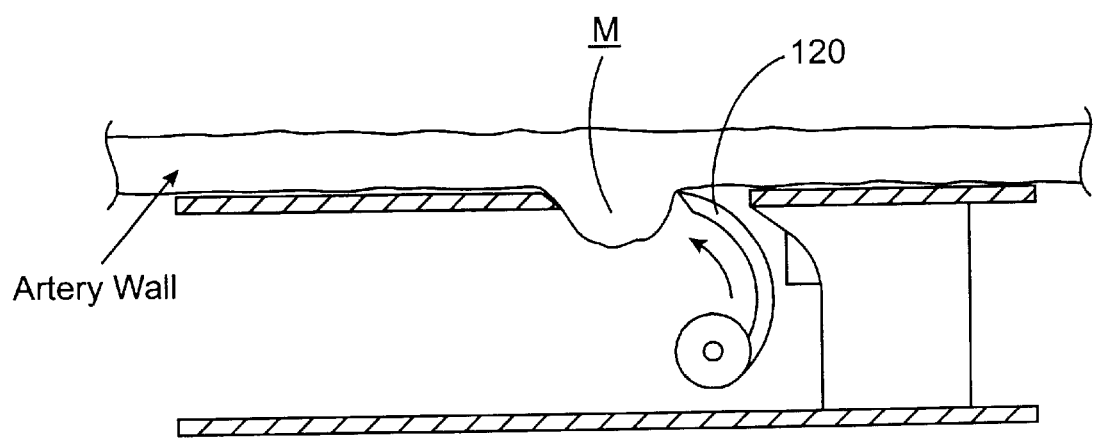

FIGS. 6A and 6B show a catheter embodiment similar to that of FIGS. 5A–5C. The material capture needle 120 of FIG. 6A rotates about a pivot 122 to engage material M to be excised from the luminal wall. The needle actuator for this embodiment differs from that of catheter 100. The material capture needle 120 of the present embodiment sits between tabs 124 and 126 which are attached to the drawbar 130. The drawbar 130 rotates the needle 120 while pulling on slider 132 having blade 134. Of course, it should be understood that the motion of the pivoting material capture needle 120 may be dependent or independent of the motion of the cutting element or blade 134. The material capture needle 120 may also be constructed of existing devices such as a suture needle used in procedures such as coronary anastomoses.

Figure 7:
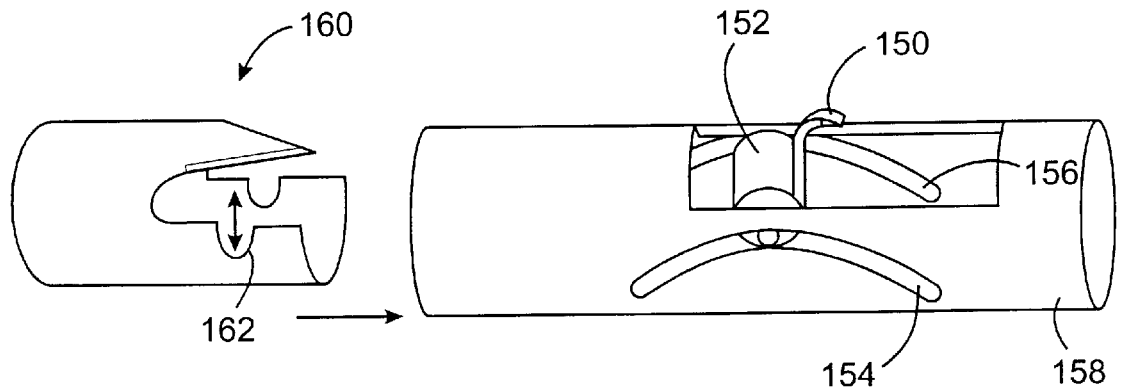
FIGS. 7–8 show still further embodiments of a material capture device and material cutting element.

FIG. 7 shows a material capture needle 150 mounted on a base 152 which slides within elongate slots or grooves 154 and 156. The slots 154 and 156 guide the needle 150 along a path that carries the needle outward and then inwardly towards the catheter body 158 after the needle has engaged the-catheter body. The inner cutter 160 has a cut-out 162 which holds the base 152 as the cutter is moved with the material capture needle 150. The base may move vertically within the cut-out 162 to follow the slots 154 and 156.

Figure 8:
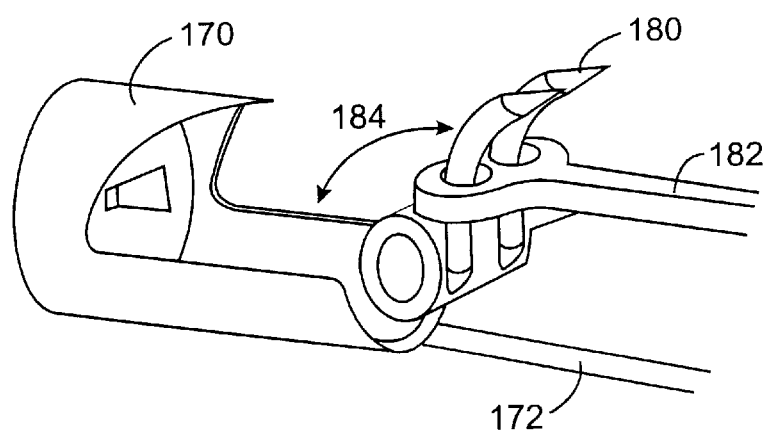

In a still further embodiment of the cutting mechanism, FIG. 8 shows a cutter 170 which is controlled by a drawbar 172 which is separate from the material capture needles 180 and drawbar 182. The material capture needles 180 continue to pivot as indicated by arrows 184. Pulling of the cutter drawbar 172 will reciprocate the cutter 170 without interacting with the positioning of the material capture needle 180. Such separate control may be desirable in particular situations where the timing of the engagement of the material capture needle 180 and the cutter 170 must be more accurately controlled.

Figure 9:
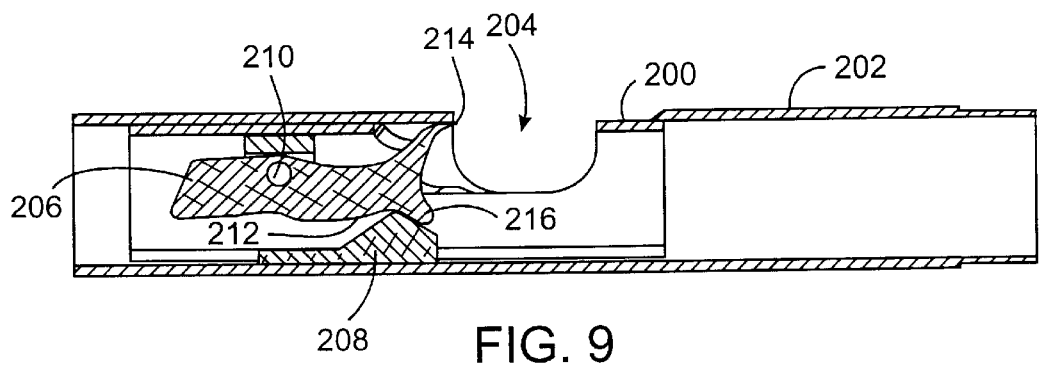
FIGS. 9–11 show cross-sectional views of a preferred embodiment of the material capture device.

Referring now to FIG. 9, a preferred embodiment of the present invention having a material capture device will now be described in further detail. FIG. 9 shows an inner cutter 200 mounted coaxially within an outer cutter 202 and in a fully distal position to open the window 204. The material capture device in this embodiment comprises a penetrating member 206 and a cam surface 208. The penetrating member 206 is pivotably mounted on the inner cutter about a pivot pin 210. The penetrating member 206 has a curved surface 212 that is designed to slide over the cam surface 208. The curved surface 212 is typically a lower or underside surface of the penetrating member 206. As the inner cutter 200 is advanced during the cutting motion, the cam surface 208 will guide the penetrating member 206 in a radially outward direction along a path that brings the member into engagement with targeted material. By varying the shape of the curved surface 212 and the height of the cam surface 208, the penetrating member 206 may have a variety of material-engaging positions, e.g., where the sharpened tip 214 extends radially beyond the outer diameter of the outer cutter 202, where the sharpened tip 214 is radially aligned with the outer diameter of the outer cutter or the inner cutter 200, or where the tip 214 is within the inner cutter. It should be understood that the curved surface 212 may be also contain longitudinal grooves and be contoured as desired to best follow and maintain contact with the cam surface 208 during the cutting motion. As shown in FIG. 9, the penetrating member 206 includes a lower protrusion 216 which helps move tissue proximally away from the cutters' after the tissue has been excised.

Figure 10:
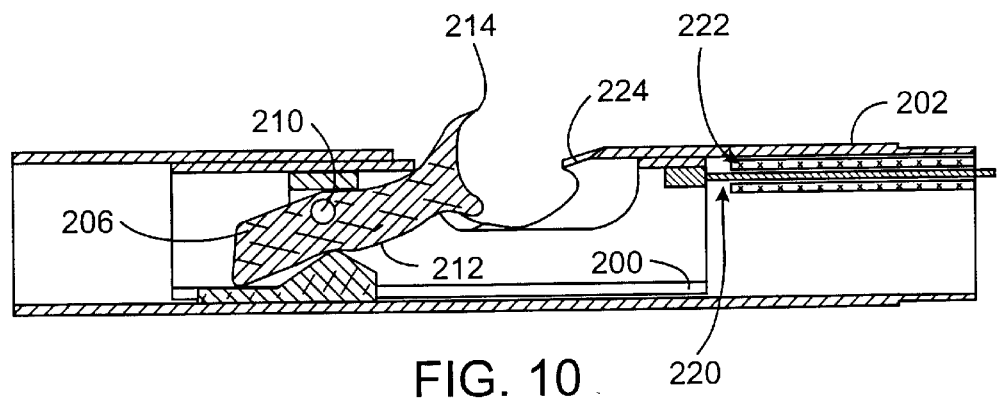

Referring now to FIGS. 10, a drive wire 220 mounted within a drive tube 222 is used to move the inner cutter 200 from a first, open position to a second, closed position. Of course, other push/pull elements or separate push elements and pull elements may be used to control the movement of the inner cutter 200. The drive wire 220 may be made of material such as stainless steel or nickel titanium. The drive tube 222 may also be made of a variety of materials such as a polymer like polyimide, polyurethane, or polyethylene or a flexible metal such as nickel titanium. The drive tube 222 may also be made from a composite of metal and polymer, or a metal that has material selectively removed to increase its flexibility. Further details of the drive tube can be found in commonly assigned, copending U.S. patent application Ser. No. 08/982,231, filed on Dec. 17, 1997, the full disclosure of which is incorporated herein by reference.

Figure 11:
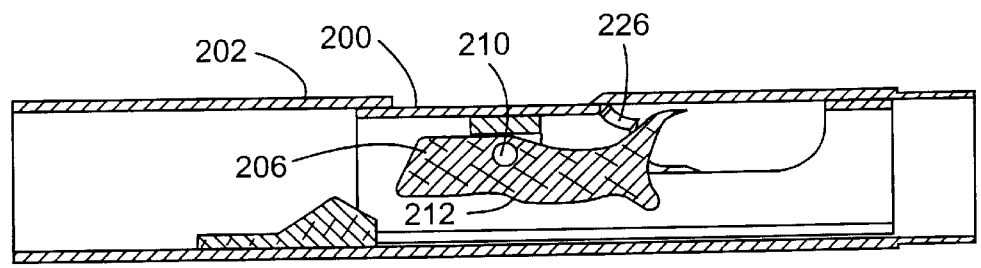

As seen in FIGS. 10 and 11, the cam surface 208 is fixedly secured to the outer cutter 202 and remains stationary relative to the penetrating member 206 during the cutting motion. The inner cutter 200 typically includes a slot or cut-out portion to accommodate the cam surface 208. Movement of the inner cutter 200 brings the sharpened end 214 into contact with target material which is pushed towards the first blade 224 (FIG. 10). Referring now to FIG. 11 as the window 204 is closed, a second blade 226 on the inner cutter 200 will complete the cutting motion by shearing off the material against the first blade 224. The cam surface 208 will push against the lower surface 212 of the penetrating member 206 and force the sharpened tip 214 of the penetrating member to retract into the inner cutter as shown in FIG. 11.

Figure 12:
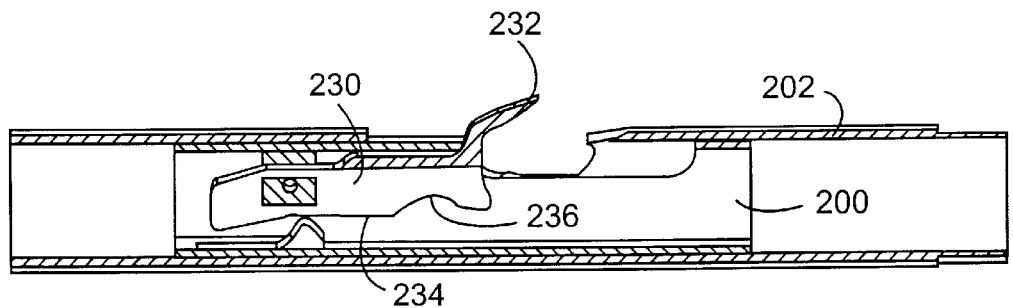
FIGS. 12, 13, 14, 14A–C, and 15 show alternative embodiments of the device show in FIGS. 9–11.
Figure 13:
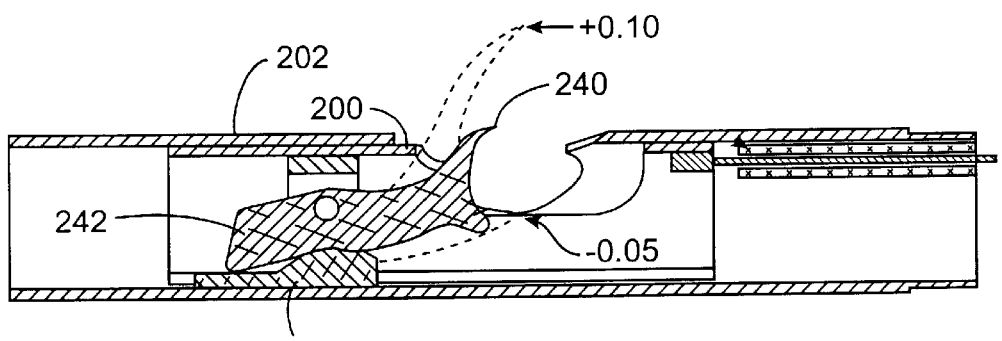
Figure 14:
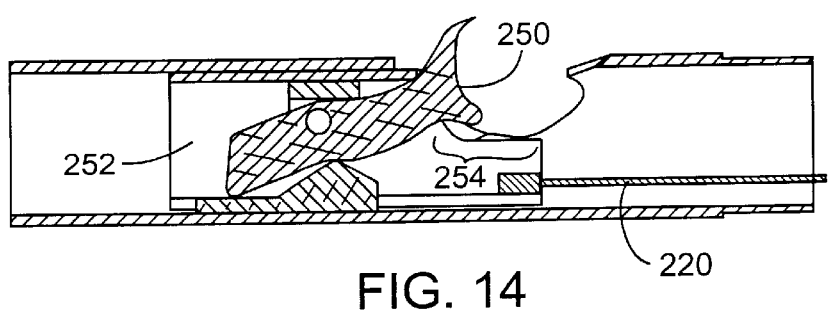

Referring now to FIGS. 12–14, other embodiments of the penetrating member, cam surface, and inner cutter will now be described. FIG. 12 shows an embodiment of the penetrating member 230 where the member has a more aggressively designed sharpened tip 232. The additional length of the tip 232 allows the penetrating member 230 to engage materials further away from the outer cutter 202. The lower surface 234 of the penetrating member 230 includes a recessed portion 236 that allows the penetrating member to be retracted into the outer cutter 202 when the inner cutter 200 is in its distal most position.

FIG. 13 shows a material capture device where the sharpened tip 240 of the penetrating member 242 is even with the outer diameter of the outer cutter 202 when the penetrating member is in its tissue-engaging position. The cam surface 244 has a decreased height and the location of the pivot pin 246 has also been lowered to change the position of the sharpened tip 240. The extension distance may vary depending on the desired function of the cutter. For example, the extension distance of the penetrating member (where the outer edge of the inner cutter is 0.000) may range between about 0.05 to 0.10 inches (as shown in phantom), preferably between about 0.00 to 0.04 inches, and most preferably between about 0.01 to 0.02 inches for a 0.100 maximum diameter cutter. The length of the sharpened tip 240 may also be used to change the maximum extension distance of the material capture device.

FIG. 14 shows an embodiment of the penetrating member 250 used with a reduced length inner cutter 252. Using a shorter inner cutter 252 can reduce the rigid length of the catheter and improve tracking of the catheter through tortuous vasculature. Unlike the inner cutters shown in FIGS. 9–11, the inner cutter 252 in FIG. 14 has the side-opening aperture 254 located at the proximal end of the cutter. In other embodiments, this side-opening aperture is located away from the ends of the cutter. Moving the aperture 254 to the end of the cutter 252 allows the reduction in rigid length. In this embodiment, the drive wire 220 is repositioned to be on the lower surface of the inner cutter 252.

Figure 14A:
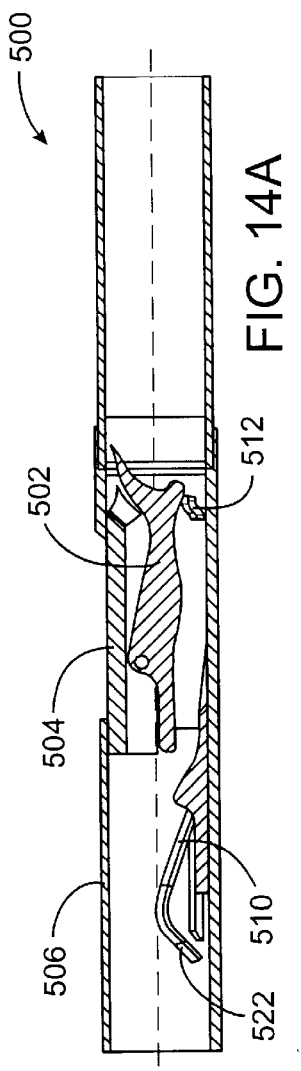
Figure 14B:
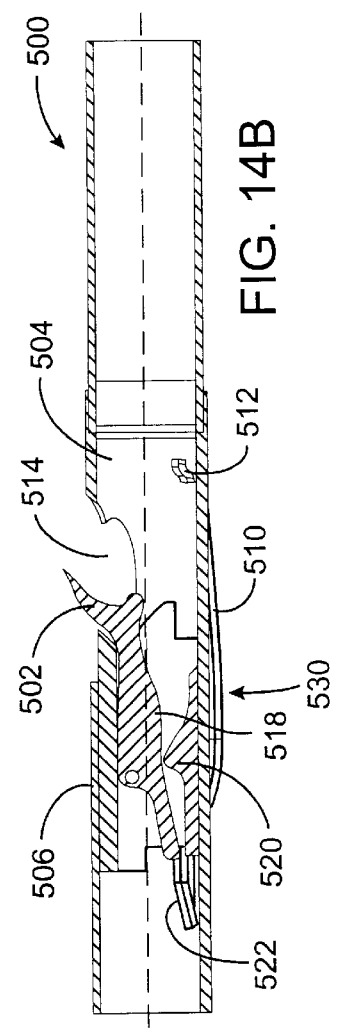
Figure 14C:
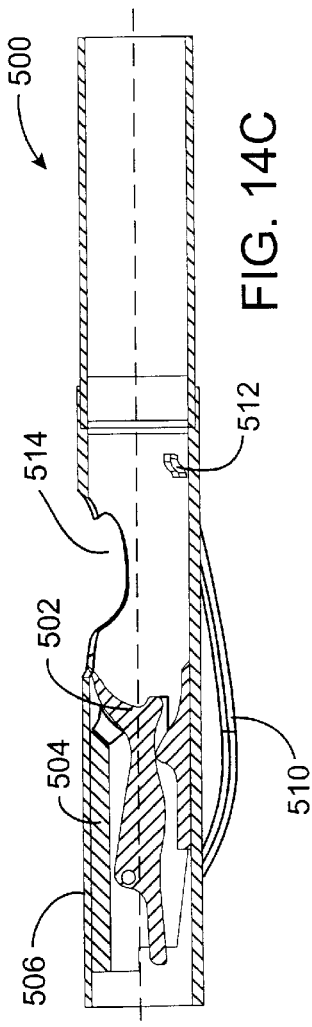

The embodiments of FIGS. 12–14 may further be provided with positioner wires as shown in FIGS. 14A–14C. The cutter mechanism 500 comprises a penetrating member 502, an inner cutter 504, an outer tubular cutter 506, and a pair of positioner wires 510 (only one of which is visible in the figures). The inner cutter 504 is shown in its closed (fully proximally advanced) configuration in FIG. 14A. The penetrating member 502 is fully radially retracted within the cutter assembly, and the positioning wires are also fully retracted.

The positioning wires 510 form from a resilient material, typically stainless steel ribbon or a shape memory alloy ribbon, such as nitinol. The proximal ends of each wire are attached in slots formed near the proximal end of the outer tubular cutter 506 and extend inwardly through openings (not shown) so that their distal ends extend radially inwardly into the interior of the outer tubular cutter, as shown in the left-hand side of FIG. 14A. With the inner cutter 504 closed, as shown in FIG. 14A, the cutter mechanism 500 can be advanced through the vasculature with a minimum profile, i.e., neither the tissue-penetrating member 502 nor the positioner wires 510 extend out from the cutter mechanism.

Once positioned at the treatment location, the inner cutting blade 504 may be distally retracted, both opening a cutter window 514 and causing the cam surface 518 on the penetrating member 502 to engage a cam element 520, causing the penetrating tip of the penetrating element 502 to emerge through the cutter window 514 as generally described with the embodiments of FIGS. 12–14. Cutter mechanism 500 differs from the earlier embodiments in that a lower portion of the inner cutter 504 engages the curved distal ends 522 of the positioner wires 510, as best seen in FIG. 14B. In particular, as the inner cutter 504 moves in a distal direction, (i.e., toward the left in FIGS. 14A–14C), it depresses the curved ends 522, causing the main body of the positioner wires 510 to emerge from the outer cutter 506, as indicated at 530 in FIG. 14B. As the inner cutter 504 moves further in the distal direction, the positioner wires 510 are deployed fully outwardly, as best shown in FIG. 14C. The cutter window 514 is fully opened and the penetrating member 502 again retracted within the cutter mechanism 500. With the positioner wires 510 fully deployed, the penetrating member 502 of the cutter mechanism is disposed to penetrate into target tissue as the inner cutter member 504 is closed in the proximal direction. Preferably, the positioner wires 510 will apply a very low amount of force against the artery wall since the penetrating member 502 will be able to quickly engage and capture the tissue to be cut by the mechanism 500. Additionally, if the lesion being treated has a small diameter, the positioner wires will simply fold over as the inner cutter is moved distally to open the cutter window 514. During the cutting operation, the positioner wires 510 will quickly spring back into the outer tubular cutter 506 since the tissue-penetrating member will act to maintain contact with the material to be cut during the remainder of the cutting operation.

Figure 15:
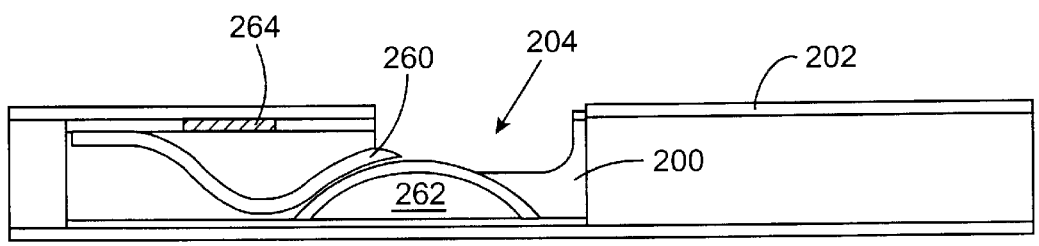

FIGS. 15–18 show a still further embodiment of the material capture device using a penetrating member and a cam surface. In FIG. 15, the penetrating member comprise a curved needle 260 which is fixedly secured to the inner cutter 200 and biased against a cam surface 262. The curved needle 260 may be integrally formed with the inner cutter 200 or otherwise attached such as by welding or other methods known in the art. As the inner cutter 200 is advanced, the cam surface 262 will guide the needle 260 along a path outwardly to engage target material and then it back towards the catheter body. As discussed previously, the needle 260 need not move beyond the outer cutter 202, instead remaining even with the outer diameter of the outer cutter as the needle engages material. The inner cutter 200 may also include a material imaging device 264 such as an ultrasound transducer or optical fibers which will image tissue when the window 204 is closed by the cutter. The optical fibers may be used for optical coherence tomography or optical coherence reflectometry. A suitable ultrasound transducer or transducer array may be found in commonly assigned, copending U.S. patent application Ser. No. 09/378,224, filed Aug. 19, 1999, the full disclosure of which is incorporated herein by reference.

Figure 16:
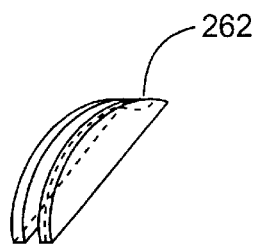
FIGS. 16–18 depict various embodiments of a cam surface according to the present invention.
Figure 17:
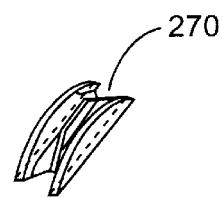
Figure 18:
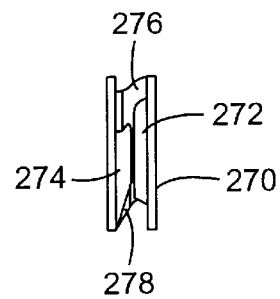

FIGS. 16–18 shows various embodiments of the cam surface 262. FIG. 16 shows a perspective view of the cam surface 262 used in the device of FIG. 15. FIGS. 17 and 18 show a cam surface 270 which has separate tracks 272 and 274 which can guide the needle 260 along different needle paths when the needle is advanced and when the needle is retracted. The cam surface 270 has funneled portions 276 and 278 for guiding the needle into the respective tracks 272 and 274, depending on whether the needle is being advanced or retracted.

Figure 19:
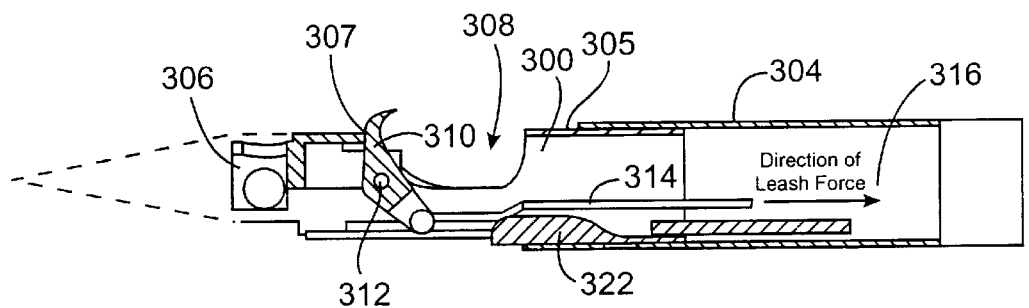
FIGS. 19–22 are cross-sectional views of a telescoping cutter having a material capture device according to the present invention.

Referring now to FIGS. 19–22, a telescoping cutting device using a material capture device will be described in further detail. As shown in FIG. 19, the telescoping portion 300 in this embodiment of the cutting device extends outwardly from an aperture 302 on the catheter body 304. The catheter body 304 may include a cutting blade 305 for shearing material drawn into the cutting device. It should be understood, of course, that the blade may be located in a variety of positions such as on the telescoping portion 300 of the device or located on both the telescoping portion and the catheter body. As shown in FIG. 19, the distal end 306 of the telescoping portion 300 is preferably adapted to mount a soft, atraumatic distal tip (shown in phantom) to facilitate passage of the device through body lumens. The tip may, in some embodiments, be integrally formed with the telescoping portion 300.

As seen in FIG. 19, the telescoping portion 300 is in a distal position where one edge 307 of the telescoping portion is spaced apart from the catheter body and defines a cutting window 308. In some embodiments, the edge 307 may comprise a cutting blade while in other embodiments the edge may be unsharpened, but pushing material into the cutting window. The cutting window 308 is preferably a directional cutting window which may open towards one side of the catheter where material may intrude to be cut off. A penetrating member 310 is preferably rotatably mounted about a pivot pin 312 on the telescoping portion 300 to engage the material. It should be understood that some embodiments of the telescoping portion 300 may not include the penetrating member 310. The penetrating member 310 is shown in FIG. 19 to be in a first, tissue-engaging position. A tether or leash element 314 is rotatably coupled to the penetrating member 310 and can be pulled proximally as indicated by arrow 316 to rotate the member into the tissue-engaging position. The tether 314 may be made of a variety of materials such as stainless steel or a polymer like polyimide or a fibrous material like Kevlar®.

Figure 20:
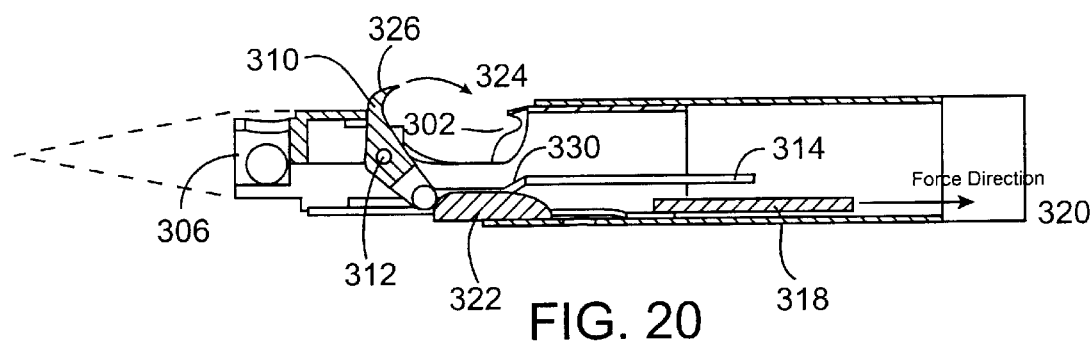
Figure 21:
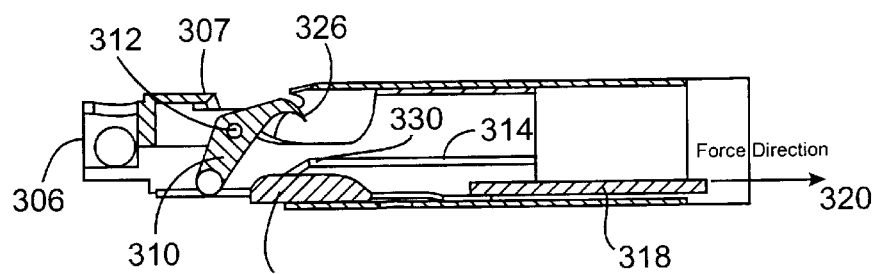
Figure 22:
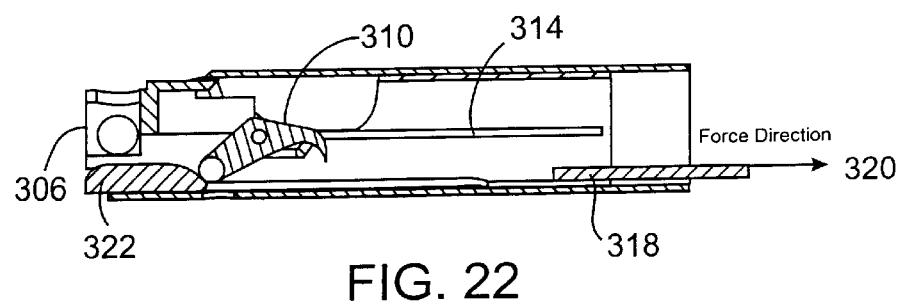

FIG. 20 shows the telescoping portion 300 being retracted by a drive wire 318 as indicated by arrow 320. As one end of the penetrating member 310 contacts abutment or deflection block 322, the penetrating member 310 will begin to rotate as indicated by arrow 324. Further retraction of the telescoping portion 300 will cause the sharpened tip 326 of the penetrating member 310 to be pushed within the boundaries of the catheter body. As seen in FIG. 21, the penetrating member 310 and telescoping portion 300 may be substantially retracted into the catheter body 304. The tether 314 has a bent portion 330 that allows the penetrating member to rotated to the position shown in FIG. 22. Retraction of the penetrating member 310 into the catheter body as shown in FIG. 22 also functions to push tissue proximally into the catheter body where it can be stored.

Figure 23:
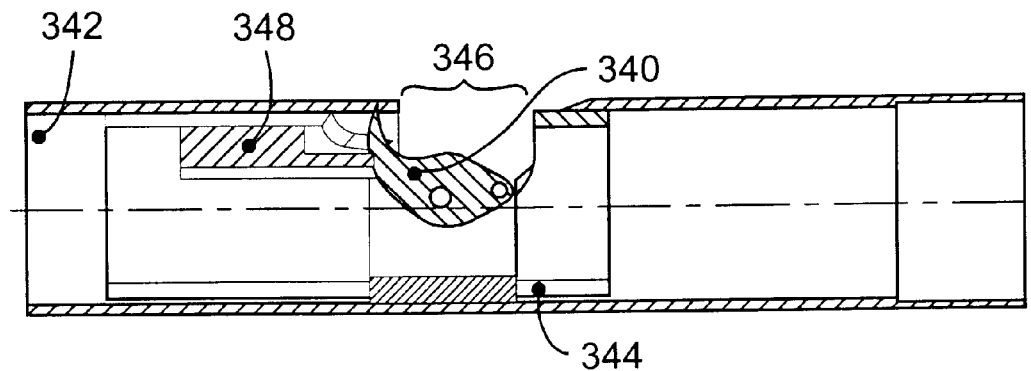
FIGS. 23–24 show a still further embodiment of the material capture device.
Figure 24:
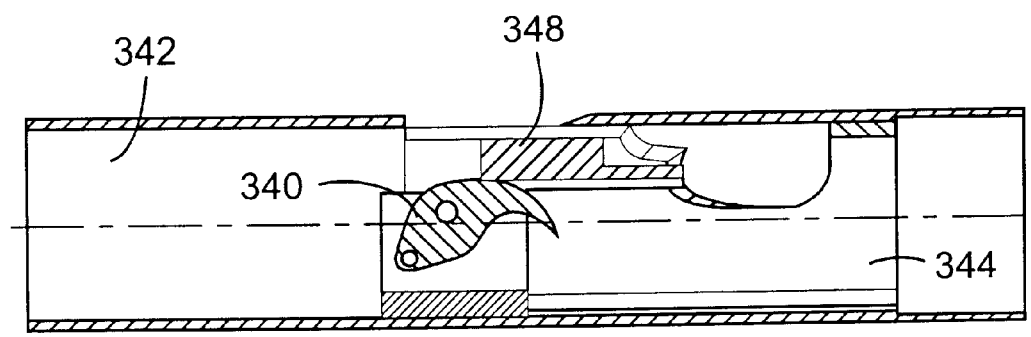

Referring now to FIGS. 23 and 24, a still further embodiment of the tissue capture device will be described. FIG. 23 shows a penetrating member 340 that is rotatably mounted to the outer cutter 342, instead of the inner, slidable cutter 344 as shown in previous embodiments. The inner cutter 344 can be reciprocated to cut off materials captured in the window 346. The inner cutter 344 includes a pushing element 348 that contacts the penetrating member 340 to rotate the penetrating member into the target material and then return to the inside of the outer cutter 342. The pushing element 348 traverses over the top of the surface of the penetrating member and wipes off any tissue, directing it into the catheter. The penetrating member 340 may be reset to its starting position by a variety of methods such as through the use of a leash element as described above or by using a bias element to create a return force.

Figure 25:
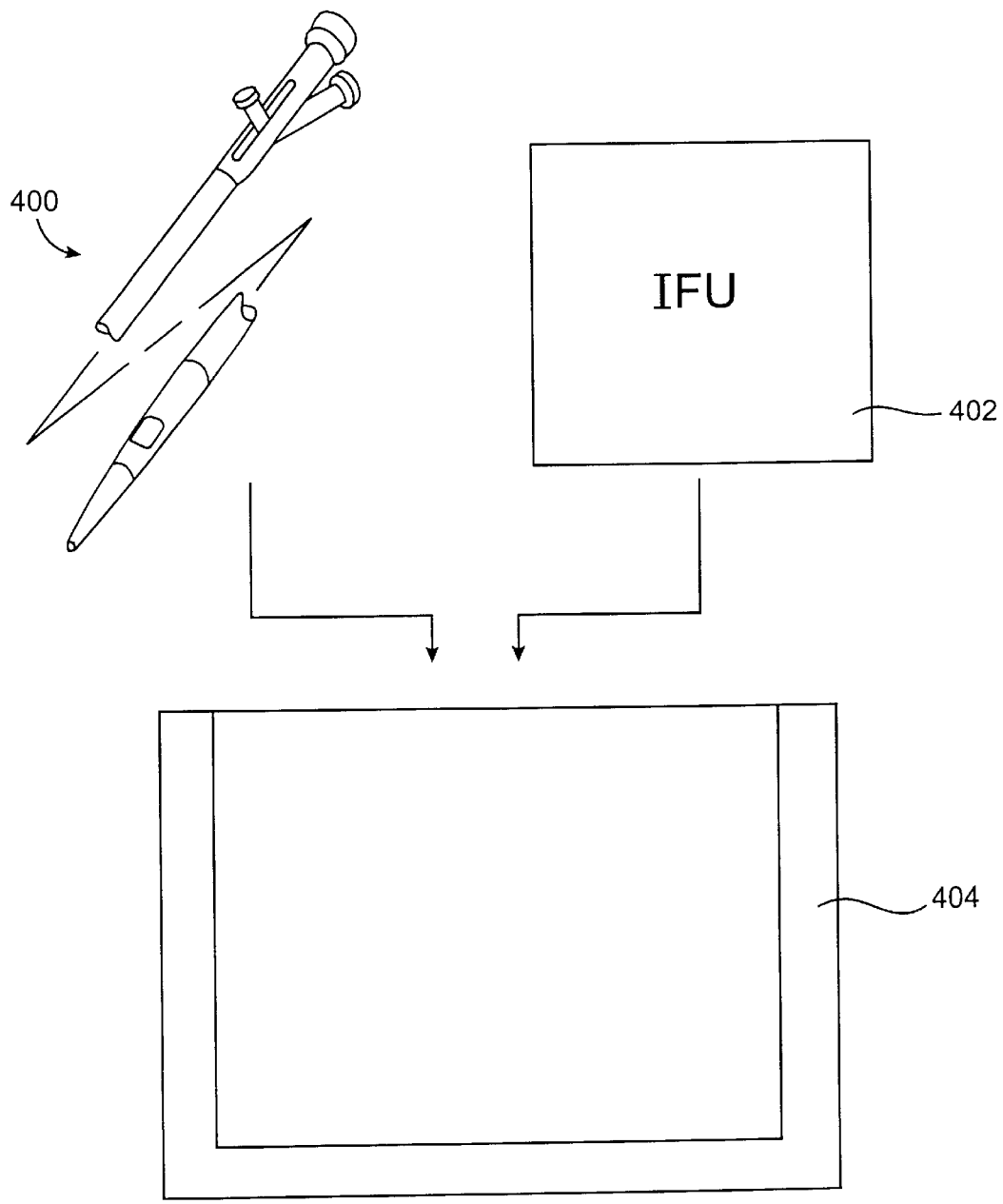
FIG. 25 shows a kit according to the present invention.

Referring now to FIG. 25, the present invention will further comprise kits including catheters 400, instructions for use 402, and packages 404. Catheters 400 will generally be described above, and the instruction for use (IFU) 402 will set forth any of the methods described above. Package 404 may be any conventional medical device packaging, including pouches, trays, boxes, tubes, or the like. The instructions for use 402 will usually be printed on a separate piece of paper, but may also be printed in whole or in part on a portion of the packaging 404.

Figure 26:
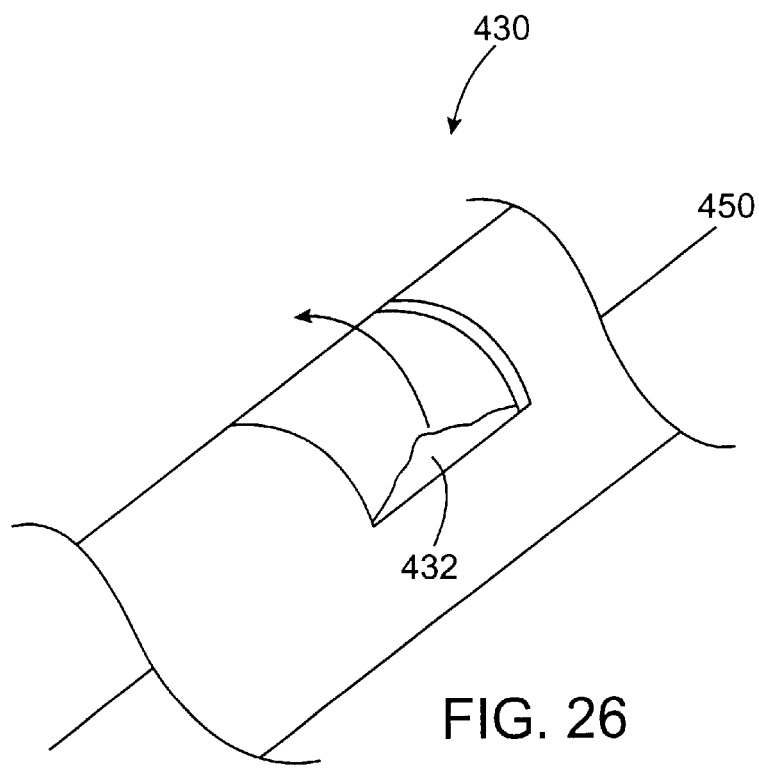
FIGS. 26 and 27 illustrate a catheter having material capture devices and material cutting elements oriented at various angles on the catheter body.
Figure 27:
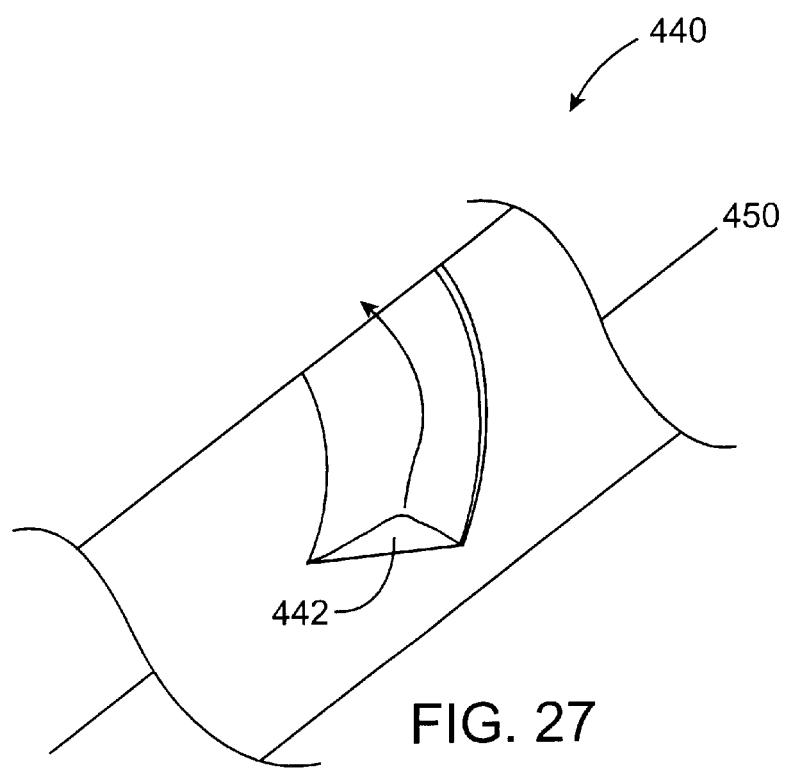
Figure 28:
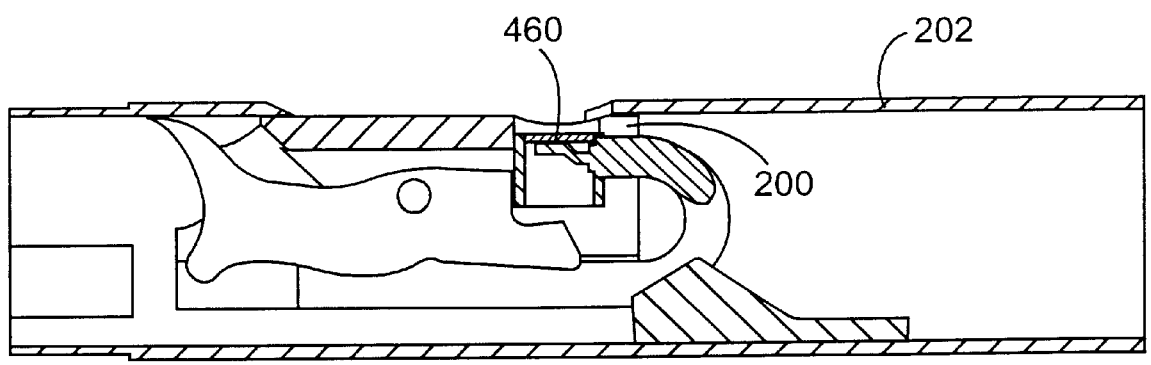
FIG. 28 shows a preferred embodiment of the present invention for use with a material imaging device according to the present invention.

While all the above is a complete description of the preferred embodiments of the inventions, various alternatives, modifications, and equivalents may be used. For example, the cutters and material capture devices may be oriented in a variety of angles on the catheter body. As seen in FIGS. 26 and 27, the catheters 430 and 440 have cutters 432 and 442 which are oriented perpendicularly or at other inclined angles to a longitudinal axis 450 of the catheter. A plurality of material capture devices may be used with a single or a plurality of cutting blades. Additionally, as discussed above for FIG. 15, another embodiment of the device includes an ultrasound transducer 460 as shown in FIG. 28. In place of an ultrasonic transducer, the device may use one or more optical fibers for optical coherence tomography or optical coherence reflectometry. Although the foregoing invention has been described in detail for purposes of clarity of understanding, it will be obvious that certain modifications may be practiced within the scope of the appended claims.

What is claimed is:

1. A catheter for removing material from a body lumen, said catheter comprising:
    a catheter body having a proximal end and a distal end;
    a material capture device arranged on said catheter body to engage said material; and
    a cutting element mounted near the distal end of the catheter body to move between a first position and a second position to cut said material while said material is engaged by said material capture device, wherein motion of the cutting element urges the material capture device to draw cut material into the catheter body;
    wherein said material capture device is coupled to the cutting element to advance along a path outwardly from the catheter body into said material and then inwardly towards the catheter body to tension said material; and
    said cutting element on said catheter body moving between said first position and said second position to cut said material while in tension.

2. The catheter as in claim 1 wherein said catheter body comprises a proximal, flexible portion and a distal, rigid portion containing said cutting element.

3. A catheter as in claim 2 wherein said catheter body comprises a inner cutter mounted coaxially within said distal, rigid portion, said material capture device mounted on said inner cutter.

4. A catheter as in claim 2 wherein said catheter body comprises an atraumatic distal tip mounted on said distal, rigid portion.

5. A catheter as in claim 1 wherein said path comprises a radially curved path extending in an outward direction away from the catheter body towards said material to be cut off.

6. A catheter as in claim 5 wherein said material capture device moving along said path does not exceed the outer diameter of the catheter body.

7. A catheter as in claim 1 wherein said material capture device travels in a slot on the catheter body to advance along said path.

8. A catheter as in claim 1 wherein said material capture device travels in a groove on the catheter body to advance along said path.

9. A catheter as in claim 1 wherein said material capture device comprises a bias element to urge said material capture device along said path.

10. A catheter as in claim 1 wherein said material capture device is configured to rotate about a pivot pin to deploy said material capture device along said path.

11. A catheter as in claim 1 wherein said material capture device comprises:
    a penetrating member pivotably mounted about a pin on said cutting element, said penetrating member movable between a first, tissue-engaging position and a second tissue-retracting position; and
    a cam surface disposed on said catheter body to contact and rotate said penetrating member about said pivot point when said cutting element is advanced over the cam surface.

12. A catheter as in claim 11 wherein said cam surface is configured to slidably contact a lower surface on said penetrating member to guide said penetrating member over an accurate path as the cutting blade is advanced.

13. A catheter as in claim 12 wherein said cam surface includes a groove for mating with said penetrating member.

14. A catheter as in claim 12 wherein said cam surface includes a first groove having a funneled opening and a second groove having a second funneled opening.

15. A catheter as in claim 12 wherein said penetrating member comprises a recess on said lower surface to facilitate positioning of said member over said cam surface.

16. A catheter as in claim 1 wherein said material capture device comprises:
    a penetrating member rotatably mounted on said cutting element; and
    an abutment disposed on said catheter body to engage one end of the penetrable member and cause rotation of the penetrating member from a first, open position to a second, closed position.

17. A catheter as in claim 16 further comprising a tether coupled to said penetrating member to control positioning of the penetrating member.

18. A catheter as in claim 1 wherein said material capture device comprises a penetrating member rotatably mounted on said catheter body and fixedly secured relative to said slidable cutting element;
    a pushing element mounted on said cutting element to engage said penetrating member to move said member between a first position to a second tissue-engaging position.

19. A catheter as in claim 1 wherein said material capture device is configured to be deployed from an aperture in the side wall of the catheter body.

20. A catheter as in claim 19 wherein said cutting element includes an material imaging device mounted to be in an imaging position when said aperture is closed by said cutting element.

21. A catheter as in claim 1 wherein said cutting element includes a first cutting blade having at least one penetrating point.

22. A catheter as in claim 1 wherein said cutting element has a first cutting blade opposed to a second cutting blade for removing said material.

23. A catheter as in claim 1 wherein said cutting element comprises a tubular inner cutter slidably mounted within an outer cutter of the catheter body, said inner cutter coupled to a drive wire actuated by a user.

24. A catheter as in claim 1 wherein said material capture device extends an extension distance outward from the catheter body to engage material, said extension distance equal to the diameter of the catheter body.

25. A catheter as in claim 1 wherein said material capture device includes a barbed distal tip to retain material on the capture device.

26. A catheter as in claim 1 wherein said cutting element further comprises a material imaging device.

27. A catheter as in claim 26 wherein said material imaging device comprises an ultrasound transducer array.

28. A catheter as in claim 1 wherein said material capture device comprises means for penetrating said material.

29. A catheter as in claim 28 wherein said means for penetrating material comprises a curved needle biased outwardly from the catheter body.

30. A catheter as in claim 28 wherein said means for penetrating material comprises a penetrating member rotatably mounted about a pivot pin on said cutting element.

31. A catheter as in claim 28 wherein said means for penetrating material is configured to engage a raised portion on said catheter body to move said means to engage material and then retract material into the catheter body.

32. A catheter as in claim 31 wherein said raised portion comprises a cam surface having a plurality of tracks, wherein each track has a funneled entrance to guide said penetrating member therein.

33. A catheter for removing material from the wall of a body lumen, said catheter comprising:
- a catheter body having a proximal end and a distal end;
- a side aperture on the catheter body;
- a cutting blade adapted to advance past the aperture to sever material which intrudes through the aperture;
- a penetration member mounted to extend through the aperture to penetrate material in advance of the cutting blade and to draw material into the catheter body as the cutting blade is advanced out of and past the aperture; and
- a cam surface mounted on said catheter body, said can surface having a surface configured to guide said penetration member out of said aperture into said material when said blade is moved.

34. A catheter for removing material from a body lumen, said catheter comprising:
- a catheter body having a proximal end, a distal end, and an aperture;
- a slidable, telescoping portion on said catheter body configured to extend outwardly from said aperture on the catheter body, said telescoping portion having a first open position leaving a gap between one edge of said portion and said catheter body to define a cutter window in which material may intrude to be engaged and having a second closed position wherein said cutting blade is positioned to cut off said material; and
- a material capture device mounted on said telescoping portion, said portion moving between a first position and a second position to cut said material while said material is engaged by said material capture device, wherein motion of the telescoping portion urges the material capture device to draw cut material into the catheter body wherein said material capture device is rotatably mounted to said telescoping portion and configured to engage a raised portion on said catheter body to rotate said material capture device to engage material and then draw material into the catheter body.

35. A method for excising occlusive material from within a body lumen, said method comprising:
- capturing said occlusive material with a material capture device on a catheter body wherein said capturing of occlusive material comprises radially extending said material capture device outward from an aperture on the catheter body;
- drawing said device radially inwardly towards the catheter body to tension the material; and
- advancing a blade through the tensioned material to sever said material from the body lumen; and
- imaging said material prior to cutting said material, wherein said imaging occurs when said aperture is closed by said cutting blade.

36. A method as in claim 35 wherein said engaging of said occlusive material comprises extending said material capture device from said catheter body in a radially outward direction.

37. A method as in claim 36 wherein said material capture device does not extend beyond the outer diameter of the catheter body when engaging said material.

38. A method as in claim 35 wherein said engaging of said occlusive material comprises penetrating said material with said material capture device.

39. A method as in claim 35 wherein said engaging of said occlusive material comprises guiding said material capture device against a raised portion on the catheter body to direct said capture device into said material.

40. A method as in claim 35 wherein said engaging of said occlusive material comprises advancing said cutting blade to engage a pushing element against said material capture device mounted on the catheter body.

41. A method as in claim 35 wherein said engaging of said occlusive material comprises penetrating said material in advance of the blade and said drawing of said device into the catheter body occurs as the cutting blade is advanced past the aperture.

42. A method as in claim 35 wherein said drawing of the device comprises moving said material capture device radially towards said catheter body while said material capture device remains in contact with said material.

43. A method as in claim 42 wherein said drawing of said material capture device occurs when said cutting element is advanced, said cutting element pushing against said material capture device and biasing it into the catheter body.

44. A method as in claim 42 wherein drawing of said material capture device comprises positioning said material capture device against a raised portion on the catheter body to guide said device with the material into the catheter body.

45. A method as in claim 35 wherein said engaging and tensioning of material are performed through a single motion by the user.

46. A method of removing material from a body lumen, the method comprising:
- advancing la catheter to a target site in the body lumen, said catheter having a catheter body with a proximal portion and a distal portion and a material removal assembly coupled with said distal portion of said catheter body;
- moving said material removal assembly from a first position to a second position to expose at least a portion of said material removal assembly through a side-opening aperture in said catheter body, wherein said distal portion of said catheter body moves relative to said proximal portion when said material removal assembly moves; and distally advancing said catheter body to penetrate said material in said body lumen with at least a portion of said material removal assembly.

47. A method as in claim 46 wherein said material removal assembly includes a cutting element, and
wherein moving said material removal assembly comprises moving said cutting element in a proximal direction within said catheter body to expose at least a portion of said cutting element through said side-opening aperture.

48. A method as in claim 47 wherein said moving said cutting element does not extend said cutting element beyond an outer diameter of the catheter body.

49. A method as in claim 47 wherein said moving said cutting element extends said cutting element beyond an outer diameter of the catheter body.

50. A method as in claim 46 wherein said moving said material removal assembly from a first position to a second position comprises extending at least a portion of said material removal assembly from said catheter body in a radially outward direction.

51. A method as in claim 46 wherein said advancing said catheter body comprises penetrating said material with at least a portion of said material removal assembly.

52. A method as in claim 46 wherein said advancing said catheter body comprises guiding at least a portion of said material removal assembly against a raised portion on said catheter body to direct said portion of said material removal assembly into said material.

53. A catheter for removing material from a body lumen, said catheter comprising:
a catheter body comprising a proximal portion, a distal portion, and a lumen extending through at least a portion of said catheter body; and
a material removal assembly movably coupled with said distal portion of said catheter body, wherein said material removal assembly is movable from a first position to a second position and wherein at least a portion of said material removal assembly is rotatable,
wherein said rotatable portion of said material removal assembly is disposed within said catheter body in said first position, and at least a portion of said rotatable portion is exposed through a side-opening aperture on said distal portion of said catheter body and extends beyond an outer diameter of said catheter body in said second position.

54. A catheter as in claim 53 wherein said rotatable portion does not extend beyond an outer diameter of said catheter body when said material removal assembly is in said second position.

55. A catheter as in claim 53 wherein said material removal assembly further comprises a bias element to expose said rotatable portion through said aperture.

56. A catheter as in claim 53 wherein said rotatable portion comprises a cutting element.

57. A catheter as in claim 53 further comprising a ramp member positioned on said distal portion of said catheter body, opposite of said side-opening aperture, wherein movement of said catheter body along said body lumen causes said ramp member to urge at least a portion of said material removal assembly into contact with said material.

58. A catheter as in claim 53 wherein said distal portion of said catheter body is movable relative to said proximal portion of said catheter body.

59. A method of removing material from a body lumen, the method comprising:
advancing a catheter to a target site in the body lumen, said catheter having a catheter body with a proximal portion and a distal portion and a material removal assembly coupled with said distal portion of said catheter body;
moving said material removal assembly from a first position to a second position to expose at least a portion of said material removal assembly through a side-opening aperture in said catheter body, wherein said material removal assembly includes a cutting element, wherein moving said material removal assembly comprises moving said cutting element in a proximal direction within said catheter body, and wherein moving said cutting element extends said cutting element beyond an outer diameter of the catheter body; and
distally advancing said catheter body to penetrate said material in said body lumen with at least a portion of said material removal assembly.

60. A method of removing material from a body lumen, the method comprising:
advancing a catheter to a target site in the body lumen, said catheter having a catheter body with a proximal portion and a distal portion and a material removal assembly coupled with said distal portion of said catheter body;
moving said material removal assembly from a first position to a second position to expose at least a portion of said material removal assembly through a side-opening aperture in said catheter body, wherein said moving comprises extending at least a portion of said material removal assembly from said catheter body in a radially outward direction; and
distally advancing said catheter body to penetrate said material in said body lumen with at least a portion of said material removal assembly.

61. A method of removing material from a body lumen, the method comprising:
advancing a catheter to a target site in the body lumen, said catheter having a catheter body with a proximal portion and a distal portion and a material removal assembly coupled with said distal portion of said catheter body, wherein said advancing comprises guiding at least a portion of said material removal assembly against a raised portion on said catheter body to direct said portion of said material removal assembly into said material;
moving said material removal assembly from a first position to a second position to expose at least a portion of said material removal assembly through a side-opening aperture in said catheter body; and
distally advancing said catheter body to penetrate said material in said body lumen with at least a portion: of said material removal assembly.

62. A catheter for removing material from a body lumen, said catheter comprising:
a catheter body comprising a proximal portion, a distal portion, and a lumen extending through at least a portion of said catheter body; and
a material removal assembly movably coupled with said distal portion of said catheter body, wherein said material removal assembly is movable from a first position to a second position and wherein at least a portion of said material removal assembly is rotatable,
wherein said rotatable portion of said material removal assembly is disposed within said catheter body in said first position, and at least a portion of said rotatable portion is exposed through a side-opening aperture on said distal portion of said catheter body in said second position, and
wherein said material removal assembly comprises a bias element to expose said rotatable portion through said aperture.

63. A catheter for removing material from a body lumen, said catheter comprising:
- a catheter body comprising a proximal portion, a distal portion, and a lumen extending through at least a portion of said catheter body;
- a material removal assembly movably coupled with said distal portion of said catheter body, wherein said material removal assembly is movable from a first position to a second position and wherein at least a portion of said material removal assembly is rotatable,
- wherein said rotatable portion of said material removal assembly is disposed within said catheter body in said first position, and at least a portion of said rotatable portion is exposed through a side-opening aperture on said distal portion of said catheter body in said second position; and
- a ramp member positioned on said distal portion of said catheter body, opposite of said side-opening aperture, wherein movement of said catheter body along said body lumen causes said ramp member to urge at least a portion of said material removal assembly into contact with said material.

* * * * *